(12) United States Patent
Kanj et al.

(10) Patent No.: US 10,047,283 B2
(45) Date of Patent: *Aug. 14, 2018

(54) CARBON-BASED FLUORESCENT TRACERS AS OIL RESERVOIR NANO-AGENTS

(71) Applicants: Saudi Arabian Oil Company, Dhahran (SA); Cornell University, Ithaca, NY (US)

(72) Inventors: Mazen Y. Kanj, Dhahran (SA); Mohammad Harunar Rashid, Ithaca, NY (US); Emmanuel Giannelis, Ithaca, NY (US)

(73) Assignees: Saudi Arabian Oil Company, Dhahran (SA); Cornell University, Ithaca, NY (US)

( * ) Notice: Subject to any disclaimer, the term of this patent is extended or adjusted under 35 U.S.C. 154(b) by 8 days.

This patent is subject to a terminal disclaimer.

(21) Appl. No.: 15/351,096

(22) Filed: Nov. 14, 2016

(65) Prior Publication Data

US 2017/0058192 A1    Mar. 2, 2017

Related U.S. Application Data

(60) Continuation of application No. 14/627,404, filed on Feb. 20, 2015, now Pat. No. 9,528,045, which is a
(Continued)

(51) Int. Cl.
*C09K 11/06* (2006.01)
*C07H 15/04* (2006.01)
(Continued)

(52) U.S. Cl.
CPC .............. *C09K 11/06* (2013.01); *B82Y 20/00* (2013.01); *C01B 32/15* (2017.08); *C07C 215/08* (2013.01);
(Continued)

(58) Field of Classification Search
None
See application file for complete search history.

(56) References Cited

U.S. PATENT DOCUMENTS 3,271,307 A    9/1966    Dickson et al.
3,292,696 A    12/1966   Sandiford
(Continued)

FOREIGN PATENT DOCUMENTS

WO    2007050984 A2    5/2007

OTHER PUBLICATIONS

Baker, S.N. and Baker, G.A., Luminescent Carbon Nanodots: Emergent Nanolights, Angewandte Chemie, (2010), pp. 6726-6744, vol. 49, Wiley-VCH Verlag GmbH & Co. KGaA, Weinheim, www.angewandte.org.
(Continued)

*Primary Examiner* — Jeffrey Washville
(74) *Attorney, Agent, or Firm* — Bracewell LLP; Constance G. Rhebergen; Brian H. Tompkins

(57) ABSTRACT

The present invention relates to carbon-based fluorescent nano-agent tracers for analysis of oil reservoirs. The carbon-based fluorescent nano-agents may be used in the analysis of the porosity of a formation. The nanoagents are suitable for injection into a petroleum reservoir and may be recovered from the reservoir for the determination of hydrocarbon flow rates and retention times.

14 Claims, 13 Drawing Sheets

Related U.S. Application Data division of application No. 13/469,459, filed on May 11, 2012, now Pat. No. 9,464,034.

(60) Provisional application No. 61/486,090, filed on May 13, 2011.

(51) Int. Cl.

| | |
|---|---|
| *E21B 47/10* | (2012.01) |
| *C09K 11/65* | (2006.01) |
| *C09K 9/02* | (2006.01) |
| *C07C 227/18* | (2006.01) |
| *B82Y 20/00* | (2011.01) |
| *C07C 235/74* | (2006.01) |
| *E21B 49/00* | (2006.01) |
| *C07C 215/08* | (2006.01) |
| *C07C 231/02* | (2006.01) |
| *C01B 32/15* | (2017.01) |
| *B82Y 40/00* | (2011.01) |

(52) U.S. Cl.
CPC .......... *C07C 227/18* (2013.01); *C07C 231/02* (2013.01); *C07C 235/74* (2013.01); *C07H 15/04* (2013.01); *C09K 9/02* (2013.01); *C09K 11/65* (2013.01); *E21B 47/1015* (2013.01); *E21B 49/00* (2013.01); *E21B 49/008* (2013.01); *B82Y 40/00* (2013.01); *C09K 2208/10* (2013.01); *C09K 2211/10* (2013.01); *Y10S 977/773* (2013.01); *Y10S 977/774* (2013.01); *Y10S 977/896* (2013.01); *Y10S 977/95* (2013.01); *Y10T 428/2982* (2015.01)

(56) References Cited

U.S. PATENT DOCUMENTS

| | | | |
|---|---|---|---|
| 4,659,676 | A | 4/1987 | Rhyne, Jr. |
| 7,505,131 | B2 | 3/2009 | Roth |
| 7,597,959 | B2 | 10/2009 | Wang et al. |
| 7,712,528 | B2 | 5/2010 | Langdon et al. |
| 7,770,646 | B2 | 8/2010 | Klassen et al. |
| 7,782,460 | B2 | 8/2010 | DiFoggio et al. |
| 7,829,772 | B2 | 11/2010 | Sun |
| 7,907,277 | B2 | 3/2011 | Csutak |
| 2001/0018503 | A1 | 8/2001 | Whipple et al. |
| 2001/0045279 | A1 | 11/2001 | Converse et al. |
| 2005/0050656 | A1* | 3/2005 | Huang .................. A61K 8/64 8/406 |
| 2008/0113448 | A1 | 5/2008 | Sun |
| 2010/0006283 | A1 | 1/2010 | Collins et al. |
| 2010/0125035 | A1 | 5/2010 | Zhang et al. |
| 2010/0148049 | A1 | 6/2010 | Csutak |
| 2010/0215760 | A1 | 8/2010 | Kundu et al. |
| 2010/0240900 | A1 | 9/2010 | Zhang et al. |
| 2010/0268470 | A1 | 10/2010 | Kamal et al. |
| 2011/0151576 | A1 | 6/2011 | Perfect et al. |
| 2012/0318503 | A1 | 12/2012 | Kanj et al. |

OTHER PUBLICATIONS

Berlin, Jacob M., et al., "Engineered nanoparticles for hydrocarbon detection in oil-field rocks", Energy & Environmental Science, vol. 4, No. 2, Dec. 3, 2010, p. 505.

Deshmukh A. A. et al: "Carbon spheres", Materials Science and Engineering R: Reports, Elsevier Sequoia S.A., Lausanne, CH, vol. 70, No. 1-2, Sep. 20, 2012, pp. 1-28.

Institute for Energy Technology: "New functional tracers based on nanotechnology and radiotracer generators" Strategic Institute Programme (SIP) 2007-2009, Sep. 17, 2007, 23 pages.

International Search Report and Written Opinion Issued in PCT Application No. PCT/US2012/037419 (SA738/PCT), dated Aug. 22, 2012; pp. 1-13.

Li, H., et al., Carbon Nanoparticle for Highly Sensitive and Selective Fluorescent Detection of Mercury (II) Ion in Aqueous Solution, Biosensors and Bioelectronics, (2011), Elsevier B.V., www.elsevier.com/locate/bios.

Li, H., et al., One-Step Ultrasonic Synthesis of Water-Soluble Carbon Nanoparticles With Excellent Photoluminescent Properties, ScienceDirect, (Oct. 29, 2010), pp. 605-609, Carbon 49, Elsevier Ltd., www.sciencedirect.com.

Mochalin, V.N., and Gogotsi, Y., Wet Chemistry Route to Hydrophobic Blue Fluorescent Nanodiamond, J. Am. Chemical Society (JACS Communications), (Jan. 26, 2009), pp. 4594-4595, vol. 131, American Cancer Society, www.pubs.acs.org.

Peng, H., and Travas-Sejdic, J., Simple Aqueous Solution Route to Luminescent Carbogenic Dots From Carbohydrates, Chemistry of Materials Communication, (Nov. 5, 2009), pp. 5563-5565, vol. 21, American Cancer Society, www.pubs.acs.org.

Sun, Y-P. et al., Doped Carbon Nonparticles as a New Platform for Highly Photoluminescent Dots, J Phys Chem C Nanomater Interfaces, (Nov. 27, 2008), pp. 18298-18298, vol. 112 (47), American Cancer Society, http://pubs.acs.org.

Sun, Ya-Ping, et al: "Quantum-Sized Carbon Dots for Bright and Colorful Photoluminescence", Journal of the American Chemical Society, vol. 128, No. 24, Jun. 1, 2006, pp. 7756-7757.

Workman Jr., J., et al., Process Analytical Chemistry, Analytical Chemistry, (Jun. 15, 2007), pp. 4345-4363, vol. 79 (12), American Cancer Society, http://pubs.acs.org.

Wang, Xin, et al: "Bandgap-Like Strong Fluoresence in Functionalized Carbon Nanoparticles", Angewandte Chemie, vol. 122, No. 31, Jun. 22, 2010, pp. 5438-5442.

* cited by examiner

CARBON-BASED FLUORESCENT TRACERS AS OIL RESERVOIR NANO-AGENTS

RELATED APPLICATIONS

This application is a continuation of and claims priority to U.S. patent application Ser. No. 14/627,404, filed Feb. 20, 2015, which is a is a divisional of and claims priority to U.S. patent application Ser. No. 13/469,459, filed on May 11, 2012, which claims priority to U.S. Provisional Patent Application No. 61/486,090, filed on May 13, 2011, the disclosures each of which are incorporated herein by reference in their entireties.

FIELD OF THE INVENTION

The present invention relates to carbon-based fluorescent nano-agent tracers for analysis of oil reservoirs, and methods of making and using same.

BACKGROUND OF THE INVENTION

Crude oil is the world's main source of hydrocarbons that are used as fuel and petrochemical feedstock. One overriding problem in exploring for hydrocarbons in the subsurface is related to the probing and characterization of an environment that cannot be seen. Similarly, after a hydrocarbon deposit has been discovered and is ready to be developed and exploited, many assumptions must be made by reservoir geologists and reservoir engineers in the modeling of a large volume of rock which cannot be seen.

Subsurface reservoir data is traditionally acquired by lowering probes into boreholes for purposes of sampling and/or probing the reservoir and from images obtained through seismography. In the first instance, the data is handicapped by the insufficiency of the resulting data, by virtue of being sourced from a single 6-inch hole, thus giving a very narrow of a view of the reservoir as a whole. Interpreted seismic volumes, on the other hand, typically give too broad of a view due to their imaging quality and resolution inadequacies. Even combining the two data types, does not enable for the mapping of exact high permeability pathways.

The integration of available geological, geophysical, petrophysical engineering, and drilling data makes interesting inroads into the detection, mapping and predictive modeling of high permeability pathways. The final uncertainty of integrated models, however, can only be marginally better than the average uncertainty inherent in each the various methods used. Mix and integrate the data as much as one may, the broad brush strokes on reservoir map deliverables will remain just that: broad brush. For example, a 0.5 mm scribble drawn on a 1:200,000 scale map to represent a fracture in the subsurface, is akin to depicting a fracture with a 200 meter aperture because of the width of the scribble relative to the scale of the map. Nor does the scribble reveal the precise path that the fluids are likely to take.

Additionally, as oil fields mature, it is expected that fluid injection for pressure support (i.e., secondary enhanced oil recovery) will increasingly tend to erratically invade and irregularly sweep the residual oil leg. Concerns have led to needs to identify, detect and map pathways that may lead injected fluids prematurely updip along encroachment fingers. More often than not, the encroachment materializes faster than even the worst case expectations, and commonly in quite unpredictable directions. Moreover, premature encroachment is commonly tortuous and will change direction in 3D volume. This type of tortuosity renders high permeability pathway prediction nearly impossible to satisfactorily pin down. In spite of an arsenal of cutting-edge technologies that can be thrown at such problems, high permeability pathway prediction capability continues to suffer from high levels of uncertainty.

Even with current technology, it is impossible to work out and predict an exact pathway that fluid fingering will take as it invades deep into an oil leg, much less where it will go next. Engineering data (e.g. water arrival data, including, water arrival detected in an oil producing well, flowmeter data, test pH build-up, pressure data, and production/injection data), although mostly acquired at the borehole, are typically correlated aerially. The resultant maps provide an indirect, unreliable and a crude way of trying to depict the geology of a reservoir. The resultant maps are interpretive, and reservoir engineers are the first to dissociate them from being accurate reflections of specific geologic features. Moreover, the map resolutions are too broad to even remotely represent most geological features that would commonly be associated with high permeability pathways.

Other interwell methods to map permeability pathways are, likewise, handicapped by resolution problems. Geophysical technologies rooted in interpreting 3D, 4D, shear wave, or multi-component volumes; even when utilizing ever-developing clarity and resolution enhancing software packages, still only render a generalized mapping of a miniscule sampling of some faults in the general area where they may or may not be located.

In carbonate rock formations, fractures having apertures that are measured in millimeters, or geobodies only centimeters across, can provide the necessary plumbing to take injected fluid past matrixed oil. To further illustrate this, a 3 cm wide fracture with no displacement may, under pressure, move fluids at several Darcies. These dimensions cannot be seen by current interpretive geophysical devices. Subsequently, the fault lines drawn on reservoir structure maps cannot be considered more than broad arrows pointing out a general direction; and not a depiction of actual permeability pathways. Furthermore, geophysically-interpreted data must be augmented by a solid understanding of the regional stress-strain regimes in order to filter out fracture swarms which may not be contributing to premature fluid breakthroughs.

Dyes and radioactive chemical tracers that can be introduced with injected fluids can be helpful locally, but generally do not reveal the actual pathway that is taken by the host fluid from the entry well to the detection well. Borehole detection methods are the most exact, but are also plagued with major shortcomings, such as for mapping purposes, wellsite data must be extrapolated and transformed into interwell information. Extrapolation in itself creates many problems. Some disadvantages associated with molecular (chemical) tracers include diffusivity and adsorption. Molecular tracers, due to their small size, tend to diffuse into all of the small pores of a matrix (as compared with larger tracers), and thus take longer periods of time to travel between the injection well and the production well. Additionally, adsorption of the molecular tracers can also be a factor, requiring the injection of much larger quantities of the chemical tracers than is desired.

The slightest shifts in water depth, measured in decimeters, can create worlds of difference in sediment deposition. Rock minerals, especially carbonates, are in continuous "life long" effective diagenesis from the instant of deposition. Carbonate porosity is dictated by deposition and unceasingly altered by diagenesis.

Geostatistical distribution of attributes, including fractures detected on borehole image logs, at the wellbore, is only statistical, and natural geological landscapes are too variable to respond comfortably to the smooth, clean logic of mathematics. There are no two features in carbonate rocks that are the same.

Nanotechnology brings new and different capabilities into upstream exploration and production. The industry desires strong, stable, friction resistant, and corrosion combatant materials in virtually all of its operations and processes (e.g., pipes, casings, drill strings, production tubings, and drill bits). These requirements are more favorably addressed with a bottom-up approach for material design and fabrication, and by employing nanofabricated particles for use in drilling, completion, stimulation, and injection fluids. Use of these materials allows faster drilling, prevents near wellbore damage, mine hydraulic fractures, plug water thief zones, reduce waterflood fingering, encourage or enhance oil production, and prevent water breakthroughs. It is hoped that the use of certain nano-based agents may soon lead to the development and deployment of sensing and intervention devices that can help delineate the waterflood front, identify bypassed oil, and map super permeability zones in-situ in the underground. The capabilities become limitless with the possibility of having functionalized molecular agents that "illuminate" the reservoir and possibly intervene to rectify adverse transport conditions in the medium.

As worldwide petroleum reserves decrease and their recovery becomes increasingly difficult, methods for locating and mapping petroleum reservoirs becomes more and more critical. Due to the high pressures and temperatures that are encountered in subsurface formations, materials that are able to withstand these conditions are needed. Thus, there is a need for the development of new materials for use with the mapping of petroleum reservoirs.

SUMMARY OF THE INVENTION

The present invention relates to carbon-based fluorescent nano-agent tracers for analysis of oil reservoirs, and methods of making and using same. In some embodiments, a fluorescent nanoagent for use in a subsurface petroleum reservoir is provided, the nanoagent including a carbon-based nanoparticle core, said nanoparticle core having an average diameter of less than about 100 nm; wherein said nanoagent includes a plurality of fluorescent functional groups appended to the surface thereof. In further embodiments, the carbon-based nanoparticle core has an average diameter of less than about 75 nm. In still further embodiments, the fluorescent nanoagent is detectable at a concentration of about 0.01 ppm. In certain embodiments, the functional groups appended the surface of the fluorescent nanoagent can be excited at a wavelength between about 400 nm and 500 nm.

In some embodiments, the functional group appended to the surface of the nanoparticle core is an amino alcohol. In further embodiments, the functional group appended to the surface of the nanoparticle core is selected from methanolamine, ethanolamine, and propanolamine. In certain embodiments, the functional group appended to the surface of the nanoparticle core is ethanolamine. In further embodiments, the functional group appended to the surface of the nanoparticle core is appended with an amide linkage. In still further embodiments, the fluorescent nanoagent is produced from a solution comprising a sugar, an amino alcohol and deionized water reacted under conditions capable of synthesizing the fluorescent nanoagent.

In some embodiments, the sugar is selected from the group consisting of glucose and fructose. In certain embodiments, the amino alcohol is selected from the group consisting of methanolamine, ethanolamine, and propanolamine. In further embodiments, the functional group is an organic functional group. In still further embodiments, the organic functional group is present in an amount of between about 50% and 90% by weight. In certain embodiments, the fluorescent nanoagent is stable at a temperature of about 100° C. to about 200° C. In some embodiments, the fluorescent nanoagent is stable at a salinity concentration of about 75,000 ppm to about 120,000 ppm.

In certain embodiments, a method for the preparation of a fluorescent nanoagent for use in a subsurface petroleum reservoir is provided. The method includes the steps of heating an aqueous mixture of citric acid and ethanolamine at a temperature of about 70° C. to remove the majority of the water and produce a viscous solution; heating the viscous solution at a temperature of at least about 200° C. for at least about 2 hr; and collecting the resulting black particles products, said particles having an average diameter of about 10 nm, and wherein said particles include a fluorescent group appended to the surface thereof.

In further embodiments, a method for the preparation of a fluorescent nanoagent for use in a subsurface petroleum reservoir is provided. The method includes the steps of heating an aqueous solution of glucose in a high pressure autoclave at a temperature of at least about 150° C. for at least about 4 hrs; adding ethanolamine to the solution and refluxing the resulting mixture for a period of at least about 10 hrs; collecting a solid product comprising carbon-based nanoparticles having fluorescent functional groups attached to the surface thereof.

In another aspect, a method for analyzing a subsurface petroleum formation is provided. The method includes the steps of injecting a fluid comprising a plurality of nanoagents prepared according to the description above into an injection well, said injection well being fluidly connected to the subsurface petroleum formation; recovering the fluid injected into the injection well at a production well, said production well being fluidly connected to said subsurface petroleum formation; and analyzing the recovered fluid for the presence of the nanoagents present therein.

In some embodiments, the fluorescent nanoagent is produced from a solution comprising a sugar, an amino alcohol and deionized water reacted under conditions capable of synthesizing the fluorescent nanoagent. In further embodiments, the sugar is selected from the group consisting of glucose and fructose. In still further embodiments, the amino alcohol is selected from the group consisting of methanolamine, ethanolamine, and propanolamine. In some embodiments, the functional group is an organic functional group. In certain embodiments, the organic functional group is present in an amount of between about 50% and 90% by weight. In some embodiments, the fluorescent nanoagent is stable at a temperature of about 100° C. to about 200° C. In certain embodiments, the fluorescent nanoagent is stable at a salinity concentration of about 75,000 ppm to about 120,000 ppm.

BRIEF DESCRIPTION OF THE DRAWINGS

So that the manner in which the features, advantages and objects of the invention, as well as others which will become apparent, are attained, and can be understood in more detail, more particular description of the invention briefly summarized above may be had by reference to the embodiments thereof which are illustrated in the accompanying drawings that form a part of this specification. It is to be noted, however, that the drawings illustrate only several embodiments of the invention and are therefore not to be considered limiting of its scope as the invention may admit to other equally effective embodiments. The present technology will be better understood on reading the following detailed description of non-limiting embodiments thereof, and on examining the accompanying drawings, in which.

DETAILED DESCRIPTION OF THE INVENTION

Although the following detailed description contains many specific details for purposes of illustration, it is understood that one of ordinary skill in the art will appreciate that many examples, variations and alterations to the following details are within the scope and spirit of the invention. Accordingly, the exemplary embodiments of the invention described herein and provided in the appended figures are set forth without any loss of generality, and without imposing limitations, relating to the claimed invention.

In one aspect, the present invention is directed carbon-based fluorescent nanoparticle tracers (hereinafter referred to as "A-Dots" and "A-NPs") as either stand-alone particles or building blocks for use in analyzing petroleum reservoirs. The nanoparticle tracers have sufficient long term stability in both high temperature and high salinity environments, allowing the tracers to survive transit through the subsurface between wells. The nanoparticle tracers can be introduced into the reservoir through an injector well, where they flow through the reservoir. They can be detected, sampled, examined and tested reliably when the nanoparticles are recovered back at the surface from a producer well. In certain embodiments, the nanoparticles can include nanosized fullerene or carbon nanotubes. In alternate embodiments, the nanoparticles are not fullerene or carbon nanotube materials. In certain embodiments, the nanoparticles can include materials having a strong fluorescence signature.

In certain embodiments, the nanoparticle tracers are stable at temperatures up to about 100° C. or greater, alternatively 200° C. or greater, and at salinity concentrations of about 75,000 ppm, alternatively about 120,000 ppm or greater in the presence of monovalent and divalent ions, such as $Ca^{+2}$, $Mg^{+2}$, and $SO_4^{-2}$. The nanoparticle tracers are also stable when in contact with the carbonate reservoir rock environment. The nanoparticle tracers of the present invention are the first reservoir nanoagents in the industry that are known to be stable under these reservoir conditions.

Figure 1:
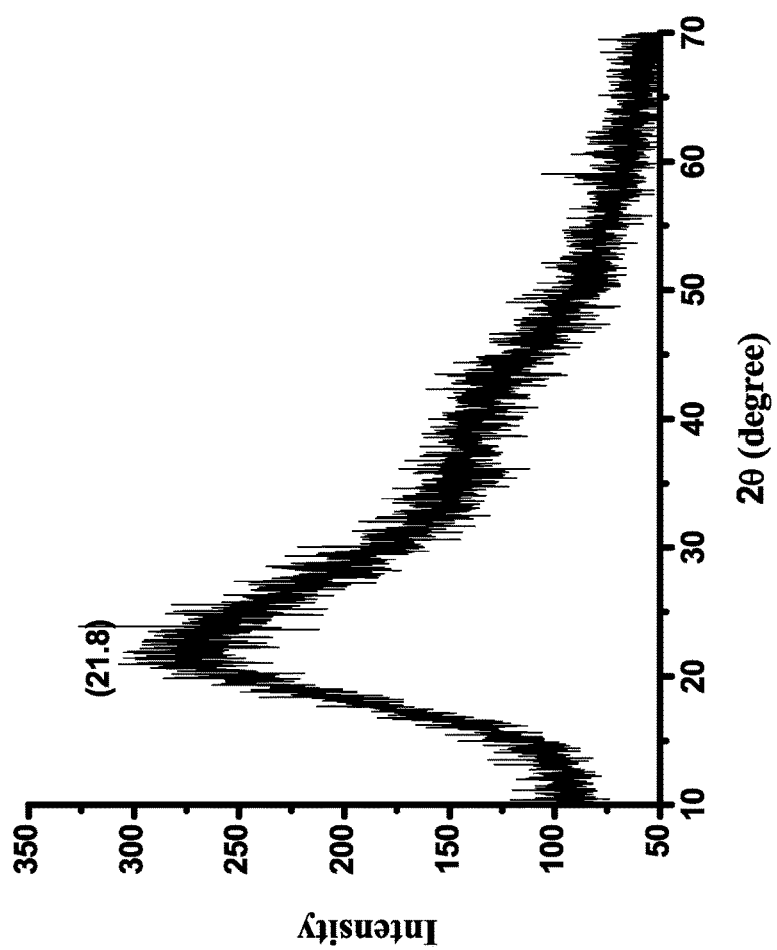
FIG. 1 provides an X-ray diffraction (XRD) pattern for one embodiment of the invention.

Carbon nanoparticles represent a unique class of nanomaterials that are typically synthesized through a hydrothermal treatment process. Analogous to their well-known cousins, fullerenes and carbon nanotubes, carbon nanoparticles can exhibit interesting optical (and electrical) properties that may be exploited in applications such as optoelectronics, chemical sensing, biological labeling, and in this case, the upstream oil and gas. For use herein, the carbon nanoparticles can have an average diameter of less than about 100 nm, alternatively less than about 75 nm, or alternatively less than about 50 nm. In certain embodiments, the carbon nanoparticles can have an average diameter of between about 10 nm and 50 nm; alternatively between about 10 nm and 30 nm. In certain embodiments the carbon nanoparticles have a diameter of between about 5 nm and 75 nm; alternatively between about 5 nm and 50 nm. An X-ray diffraction (XRD) pattern of the A-Dots is shown in FIG. 1. The pattern shows the characteristics of a poorly crystalline graphite structure at $2\theta=21.8°$, with (002) interplanar spacing of 4.2 Å.

The A-Dots and A-NPs described in certain embodiments herein are passive reservoir carbon nanoparticle-based nanoagents that target reservoirs for in-situ sensing and intervention. Exemplary intervention activities can include acting to rectify unfavorable oil sweep and recovery conditions existing in a reservoir, such as plugging super-permeable zones for enhanced conformance during waterfloods or for delivering chemicals to targets deep within a reservoir to alter wettability, reduce interfacial tensions, and/or enhance oil recovery. It is understood that the carbon nanoagents described herein can be used for other intervention activities beyond the exemplary activities listed above. In-situ sensing and intervention is a highly appealing concept for analyzing petroleum formations. In view of the severe reservoir conditions of temperatures of up greater than about 100° C. and salinity concentrations of up to about 120,000 ppm or greater, a fundamental challenge in utilizing nanoparticle tracers to determine formation properties and conditions is the stability of the nanoagents in the subsurface medium.

As the A-Dots and A-NPs are the first nanoparticles in the industry (currently in passive form) that have proven stability in subsurface conditions, these nanoparticles may, in certain embodiments, also provide a template or design that become basis for the preparation of functional active and/or reactive nanoagents. One possible use is with the nanoagents disclosed in U.S. Ser. No. 12/722,357, filed on Mar. 11, 2010, which claims priority to U.S. Prov. Pat. App. Ser. No. 61/159,943, filed on Mar. 13, 2009.

As noted previously, one important unique feature of both the A-Dots and the A-NPs is their in-reservoir stability. More specifically, both the A-Dots and A-NPs have been found to be stable at temperatures of between about 100° C. and 150°

C., and greater, and also in a brine solution that includes the following compounds at the following concentrations: NaCl (128.9 g/L), $CaCl_2 \cdot 2H_2O$ (109.16 g/L), $MgCl_2 \cdot 6H_2O$ (35.66 g/L), $BaCl_2$ (0.02 g/L), $Na_2SO_4$ (0.16 g/L) and $NaHCO_3$ (0.48 g/L), totaling a concentration of about 120,000 ppm of total dissolved solids. Generally, the A-Dots and A-NPs have been found to be stable in water, alternatively in brine solutions having a total dissolved solids concentration of between 100 ppm and 25,000 ppm, alternatively in brine solutions having a total dissolved solids concentration of between 25,000 ppm and 50,000 ppm, alternatively in brine solutions having a total dissolved solids concentration of between 50,000 ppm and 100,000 ppm, alternatively in brine solutions having a total dissolved solids concentration of greater than 100,000 ppm. Stability has also demonstrated in connate water having a concentration of 220,000 ppm TDS.

To gauge the A-Dots adsorption potential and affinity to carbonate rock formations, ample amounts of either crushed limestone (coarse grain) or $CaCO_3$ powder were used. Small amounts of oil from the Arab-D reservoir were also added to gauge the hydrophilicity of the nanoparticles. The samples were shaken and heated to a temperature of up to about 150° C. for up to 12 days. Fluorescence spectra were measured before and after each test. According the Arrhenius law, accelerated testing at about 150° C. increased the exposure time 32-fold for the target reservoir temperature of about 100° C.

Figure 2:
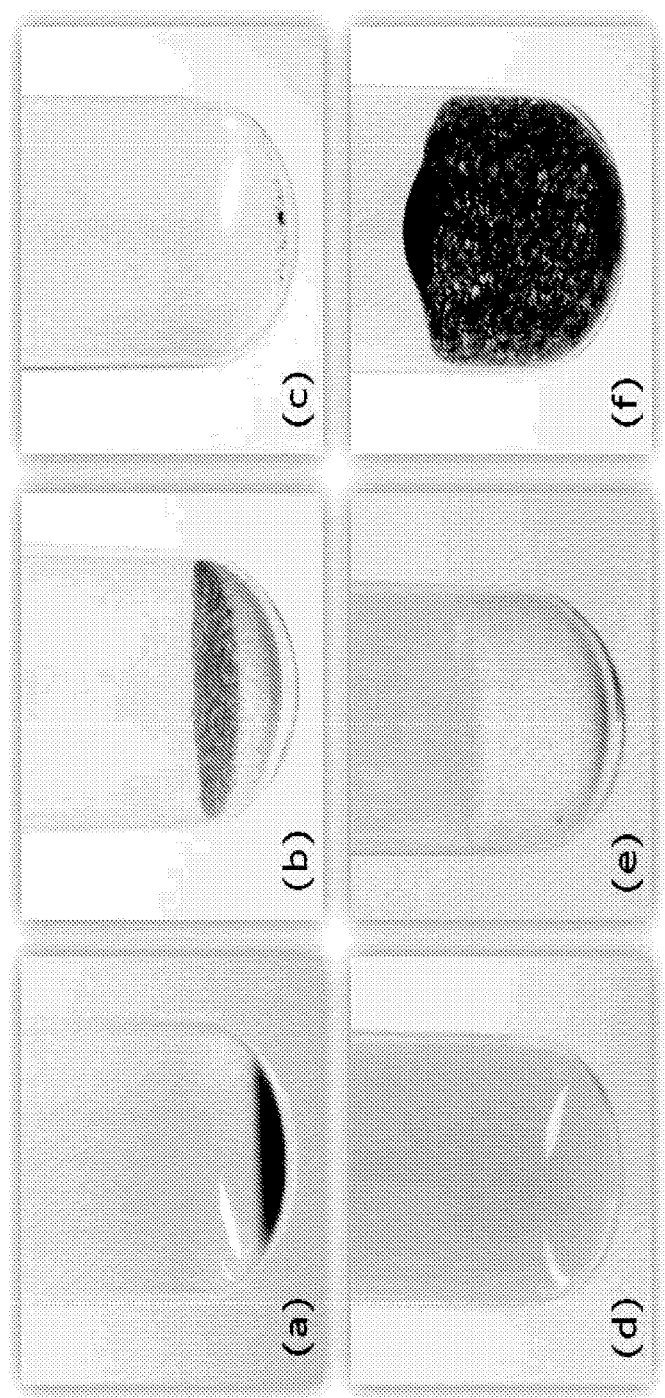
FIG. 2 provides a comparison of stability of one embodiment of the invention as compared with a control sample.

The results showed A-Dots to be stable at high temperatures and high salinity conditions for very long durations (i.e., for up to about 12 days at 150° C.). The A-Dots also maintained strong fluorescence after exposure to high temperatures and high salinity conditions with no discernible particle aggregation (as shown by TEM). The A-Dots also remained colloidally stable, even after centrifugation, with no visible sedimentation or loss of fluorescence. Referring to FIG. 2, the importance of proper surface functionalization on the nanoparticle stability is shown. As used herein, proper functionalization refers to the introduction of functional groups to the surface of the nanoparticles that allows the particles to remain dispersed and suspended, and without having an affinity to stick or bind to carbonate present in the reservoir environment. Suitable functional groups generally include primary amines and primary amino alcohols. One such exemplary amino alcohol is ethanolamine. In certain embodiments, methanolamine and propanolamine can also be used. In certain embodiments, secondary amines or alcohols can be used. In other embodiments, the functional groups can be selected based upon their ability to exhibit high fluorescent yields, and may be selected based upon the reactivity of the fluorescent functional groups with a formation. In certain embodiments, the organic functional groups are present in an amount of between about 50% and 90% by weight, alternatively between about 60% and 80% by weight, alternatively between about 70% and 80% by weight, alternatively between about 65% and 75% by weight.

FIG. 2 shows a comparison of the stability of the A-Dots nanoparticle system to a typical nanoparticles solution (for example, a 100 ppm or 100 ppm solution of non-functionalized nanoparticles) following thermal treatment for about 5 days at a temperature of about 120° C. in high salinity brine (i.e., at least about 120,000 ppm TDS). Tests were conducted under similar conditions for the two nanoparticle solutions. As shown in FIG. 2, ethanolamine functionalized A-Dots at a concentration of about 1000 ppm remained stable over the course of the test, as depicted in FIGS. 2d and 2e. In contrast, as shown in FIGS. 2a and 2b, greater amounts of flocculation and sedimentation occur for a solution having a 1000 ppm concentration of nanoparticles that have been functionalized with JEFFAMINE®. FIG. 2c shows sedimentation following a second cycle of heat treatment on the supernatant from the sample in FIG. 2b. Colloidal stability and hydrophilicity testing in the presence of hot brine, $CaCO_3$ fines, and Arab-D oil for the A-Dots is presented in FIG. 2f.

Figure 3:
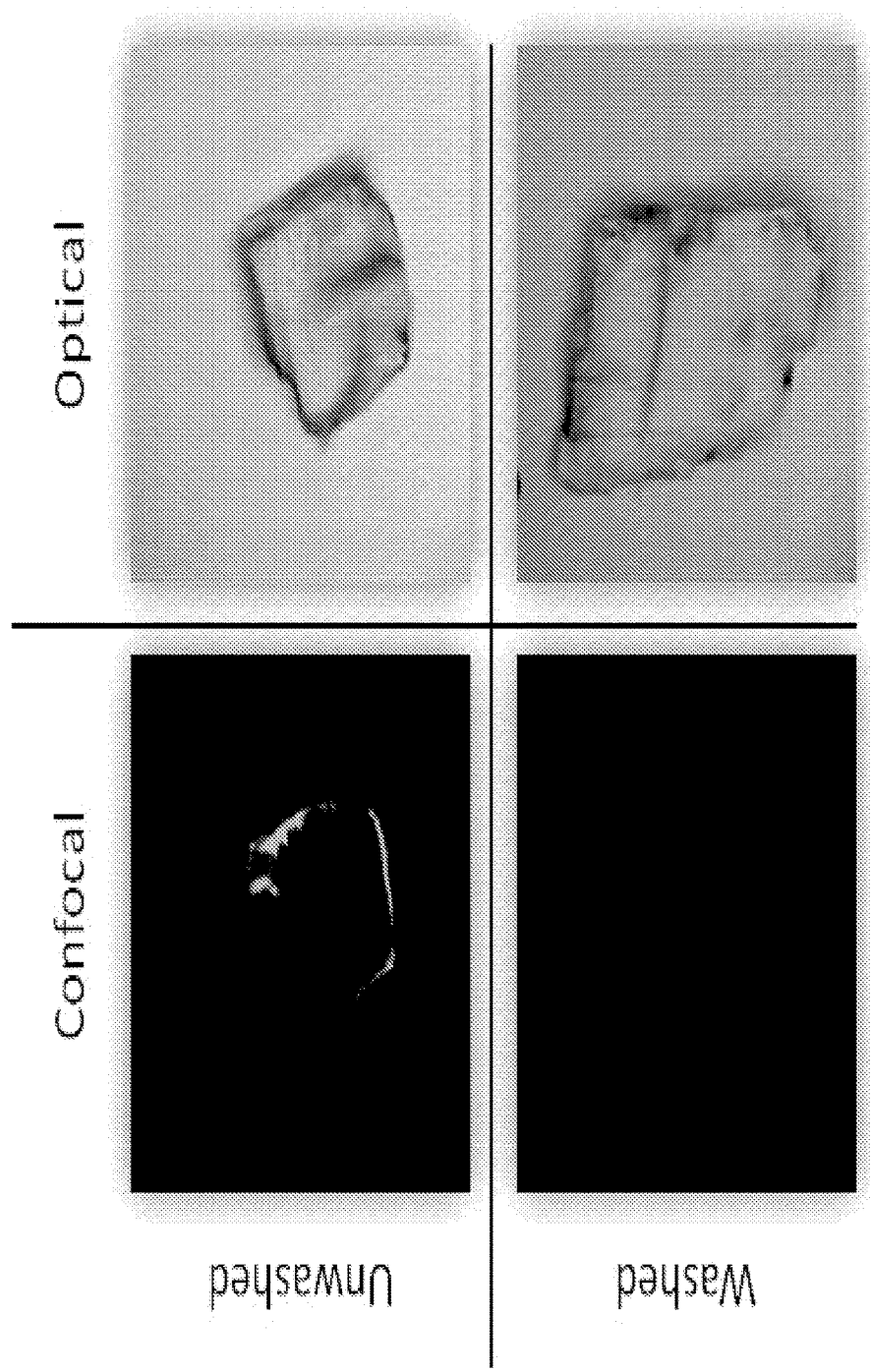
FIG. 3 provides a comparison of washed and unwashed samples of one embodiment of the present invention using optical and confocal microscopy.

FIG. 3 shows carbonate crystals under both optical and confocal microscopy for the same crystal following exposure to A-Dots solution, providing the affinity of the A-Dots to the carbonate crystals. The unwashed crystals are clearly visible under confocal microscopy due to the residue of the fluorescent A-Dots; whereas, the washed crystals are not. This demonstrates that the A-Dots are not stuck or bonded to the carbonate crystals, but are instead merely sitting on them, thus indicating a likelihood that the A-Dots will travel through carbonate formations.

A-Dot fluorescence is high and, in certain embodiments, can be detectable at levels below about 5 ppm, alternatively at levels below about 1 ppm, alternatively at levels below about 0.5 ppm, alternatively at levels below about 0.1 ppm, or at levels below about 0.05 ppm. In certain embodiments, it is possible to detect the presence of A-Dots at concentrations as low as 1 ppb (i.e., 0.001 ppm). Fluorescence quantum yield (i.e., photons emitted/photons absorbed) can be about 10%, and is virtually independent of the excitation wavelength, which can be in the range of between about 400 to 500 nm. Emission is preferably monitored at a wavelength of about 460 nm, although it is possible to monitor the emission at other wavelengths as well. In certain embodiments, upon excitation, the A-Dot fluorescence can be detected at a wavelength of between about 450 nm to about 475 nm.

Figure 4:
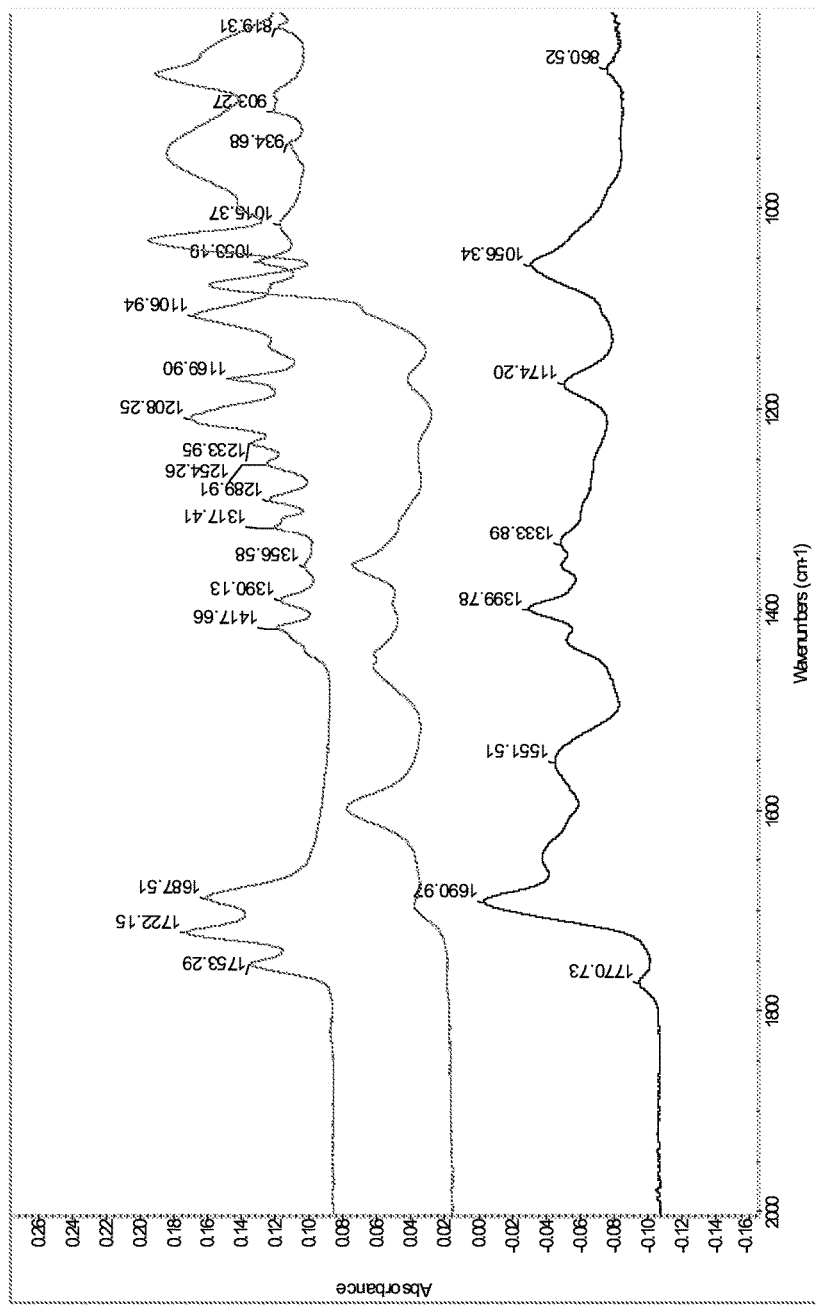
FIG. 4 provides a Fourier transform infrared spectroscopy (FTIR) spectrum of one embodiment of the present invention.

In certain embodiments, the intensity of the fluorescence is not affected by the presence of $CaCO_3$, demonstrating that use in carbonate formations does not reduce the fluorescence of the tracers. Without wishing to be bound by any single theory, fluorescence is believed to depend upon the formation of amide linkages on the surface of the carbon nanoparticles, which may be responsible for the majority of the fluorescence. This is shown in FIG. 4, which shows an FTIR spectrum (bottom trace) of one embodiment of the A-Dots, wherein peaks at about 1690 cm-1 and 1550 cm-1 are characteristic of the presence of amide linkages. The top trace is the FTIR spectra of citric acid, and the middle trace is the FTIR spectra of ethanolamine.

A-Dot solubility was tested in deionized water, seawater (having a concentration of about 50,000 ppm TDS), high salinity brine (having a concentration of about 120,000 ppm TDS), and super-high salinity brine (having a concentration of about 230,000 ppm TDS) at temperatures of between about 100° C. and 150° C.

In general, the A-Dots can be synthesized in a simple, one-pot reaction. Carbon nanoparticles are produced hydrothermally, followed by surface functionalization. Accordingly, the process is very amenable for scale-up to the kilogram level in a non-industrial research lab environment. The synthesis is also very economical, with a current cost of less than about $10.00/kg. As the A-Dots can be detected at concentrations that are below 100 ppb concentrations, the labeling injection water with the A-Dots to a level of about 10 ppm (which is 100 times greater than the minimum detection limit of the A-Dots) can be done at a current cost of about $20.00 per thousand barrels of injection water, which is several orders of magnitude less expensive than conventional molecular tracers that are currently being used.

In contrast, the larger A-NPs carbon nanoparticles can be prepared in a two-step process. The synthesis of the A-Dots and A-NPs proceeds as follows.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Chemicals:

Ethanolamine (99%), citric acid monohydrate (99.5%), glucose (anhydrous), NaCl (99%), $MgCl_2 \cdot 6H_2O$, $CaCl_2 \cdot 2H_2O$ (99%), $BaCl_2$ (99.9%), $Na_2SO_4$ (99%) and $NaHCO_3$ (99.7%) were purchased from Sigma-Aldrich and were used as received without further purification.

Characterization:

TEM images were obtained using a Tecnai FEI T12 transmission electron microscope operated at 120 kV. Samples were prepared by placing a small drop of an aqueous suspension on a carbon-coated copper grid. Excess solution was wicked off using a blotting paper. The grid was then dried in air prior to imaging. Dynamic Light Scattering and zeta potential measurements were carried out using a Malvern Zetasizer (Malvern Instruments, Nanoseries). Each sample was measured three times and the average value was used. Photoluminescence spectra were obtained using a Molecular Device Spectra Max $M2^e$ spectrophotometer equipped with a xenon flash lamp. The excitation wavelength was 385 nm.

Example 1

Synthesis of A-Dots (Carbon-dots). In a typical process, 4.2 g citric acid monohydrate and 3.66 g ethanolamine were dissolved separately in 10 mL of deionized water and mixed using a magnetic stirrer. The reaction mixture was then heated to about 70° C. on a hot plate under constant stirring to evaporate the majority of the water from the reaction mixture. When the reaction mixture became syrupy, the magnetic bar was removed and the reaction mixture was placed in a furnace and heated of at least about 200° C. in air at a rate of 10° C./min for at least about 3 hrs. The resulting black product was allowed to cool to room temperature and used without any further purification. The products are highly soluble/dispersible in water.

In certain embodiments, the synthesis of the A-Dots leads to uniformly sized hybrid nanoparticles (hairy) that are readily dispersible in water and organic solvents, depending upon the length and type of ligands that are attached to the carbon core.

Figure 13:
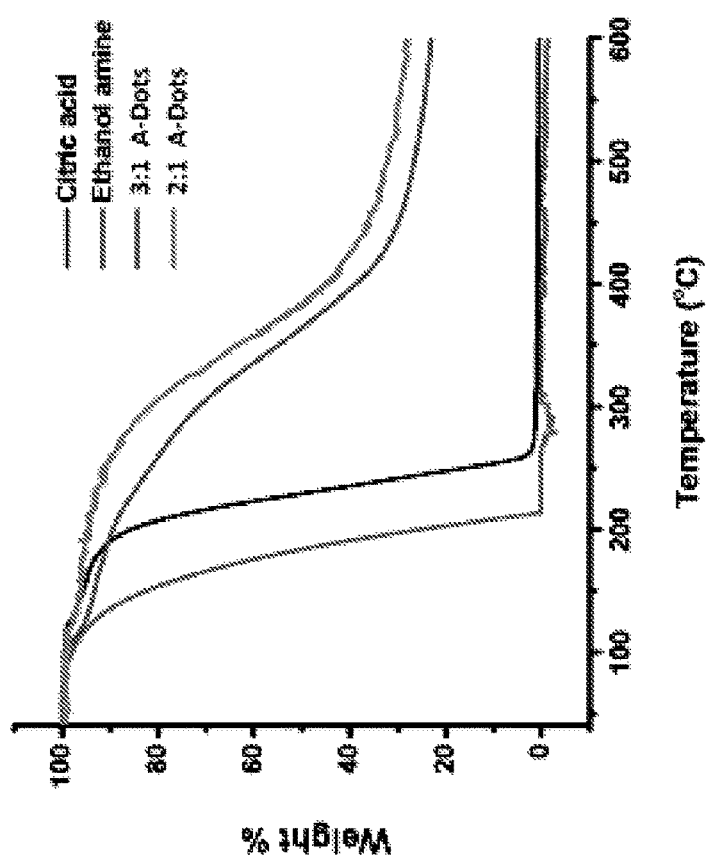
FIG. 13 provides a thermogravimetric analysis (TGA) of one embodiment of the present invention.

The amount of organic compound present on the surface as determined by thermogravimetric analysis (TGA) and shown in FIG. 13 is approximately 75% by weight. From left to right, FIG. 13 shows the TGA of ethanol amine, citric acid, 3:1 A-Dots and 2:1 A-Dots.

Example 2

Scale up Synthesis of A-Dots (Carbon-dots). For the scale up synthesis of A-Dots, 378 g of citric acid monohydrate and 330 g of ethanolamine were separately added to two large beakers and combined with enough deionized water was added to each to bring the volume to 900 mL. After complete dissolution, the ethanolamine solution was added to the citric acid solution under constant magnetic stirring. The mixture was stirred and heated at 70° C. on a hot plate to evaporate most of the water. After the volume was reduced to about 650 mL, the mixture was transferred to 1 L glass bottles and heated at 200° C. in air at a rate of 10° C./min for 8 hrs.

Example 3

Figure 5:
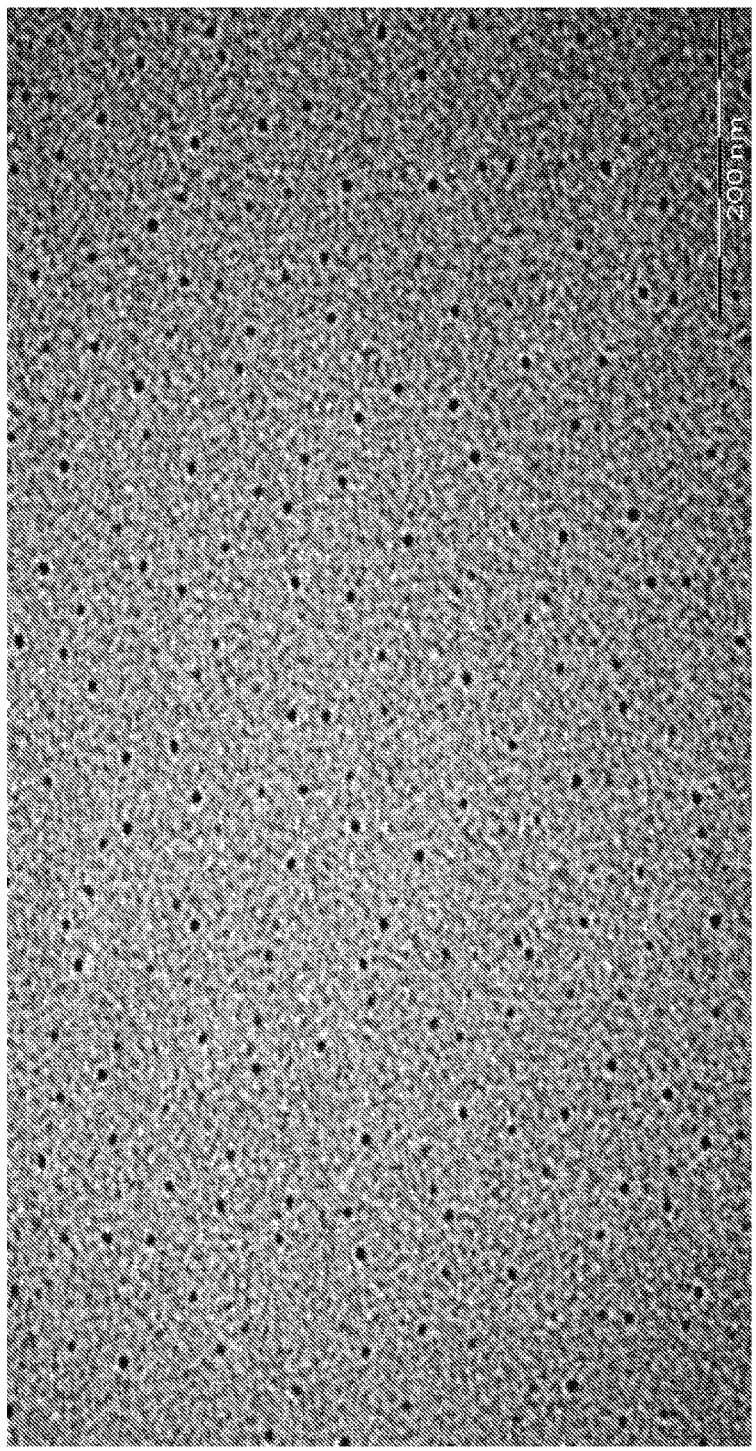
FIG. 5 provides a transmission electron microscopy (TEM) image of one embodiment of the invention.
Figure 6:
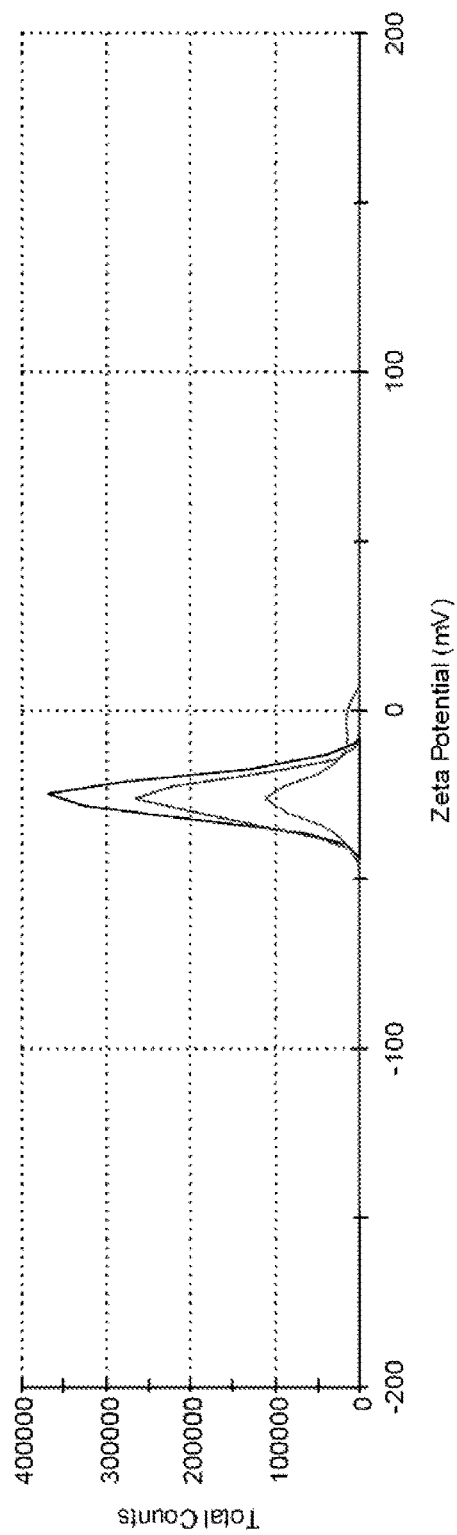
FIG. 6 provides a measure of the zeta-potential of one embodiment of the invention.

Characterization of A-Dots. The carbon-dots were synthesized via a one-pot reaction using the citrate salt as a precursor. When citric acid and ethanolamine are mixed, the corresponding ammonium carboxylate salt is formed. During pyrolysis, the citrate part of this precursor molecule provides the source of carbon for the core with the remaining ammonium groups attached to the surface. The reaction leads to uniform size hybrid (hairy) nanoparticles in high yield that are readily dispersible in water or organic solvents, depending on the type and length of ammonium hairs attached to the carbon core. Referring to FIG. 5, TEM images of the carbon-dots prepared from an aqueous solution show uniform particles having an average diameter of less than about 10 nm. Referring now to FIG. 6, the resulting nanoparticles are negatively charged having a zeta potential of about −26 mV. Without wishing to be bound by any single theory, the negative charge and zeta potential are possibly due to the presence of carboxylate groups on the surface of the nanoparticles.

Figure 7:
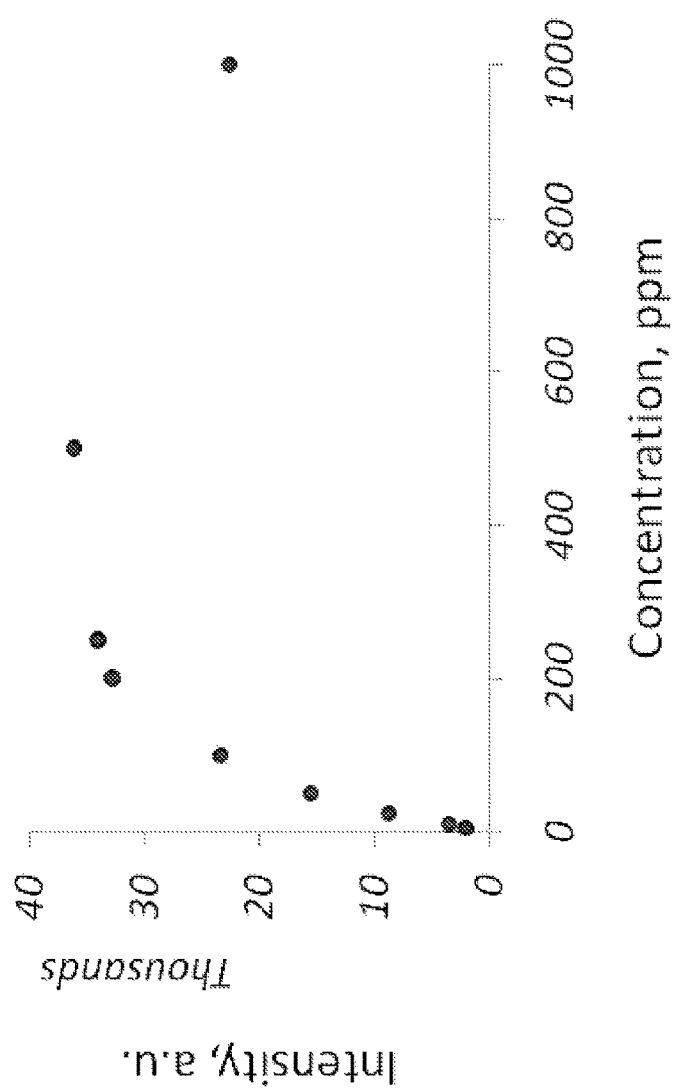
FIG. 7 provides the fluorescence measure of one embodiment of the invention.

Referring to FIG. 7, the carbon-dots are highly fluorescent and can be detected at concentrations below 2 ppm, alternatively at concentrations less than about 1 ppm, alternatively at concentrations of about 0.1 ppm, alternatively at concentrations of about 0.01 ppm, or alternatively at concentrations of about 0.001 ppm. FIG. 7 shows that above certain concentrations of the carbon A-dots, the fluorescence intensity becomes saturated and starts decreasing due to self-quenching. The fluorescence quantum yield of the A-Dots is approximately 10% and is virtually independent of the excitation wavelength within the range of 400-500 nm, thus making the A-Dots excellent emitters that are detectable at relatively low concentrations.

Example 4

A-NP (Carbon Nanoparticles) Synthesis. Carbon nanoparticles were synthesized by hydrothermal treatment. In a typical reaction, 0.61 g of glucose was dissolved in 17 mL of deionized water, although other sugars, such as fructose, can be used. The resulting solution was then transferred to a high pressure stainless steel autoclave fitted with a glass liner and sealed. The reactor was heated to 160° C. in an oven for 4 hrs at a heating rate of 10° C./min. After cooling a dark brown solution was obtained and used without further purification. For surface functionalization, approximately 20 mL of the solution was transferred to a round bottom flask fitted with a condenser and diluted to 80 mL with deionized water. Approximately 4 mL of an aqueous solution containing about 0.8 mL of ethanolamine was added to the flask and the mixture was refluxed for approximately 12 hrs. After cooling to room temperature, the resulting products were purified by dialysis in water using a cellulose membrane (having a molecular weight cut-off of 7000).

Example 5

Figure 8:
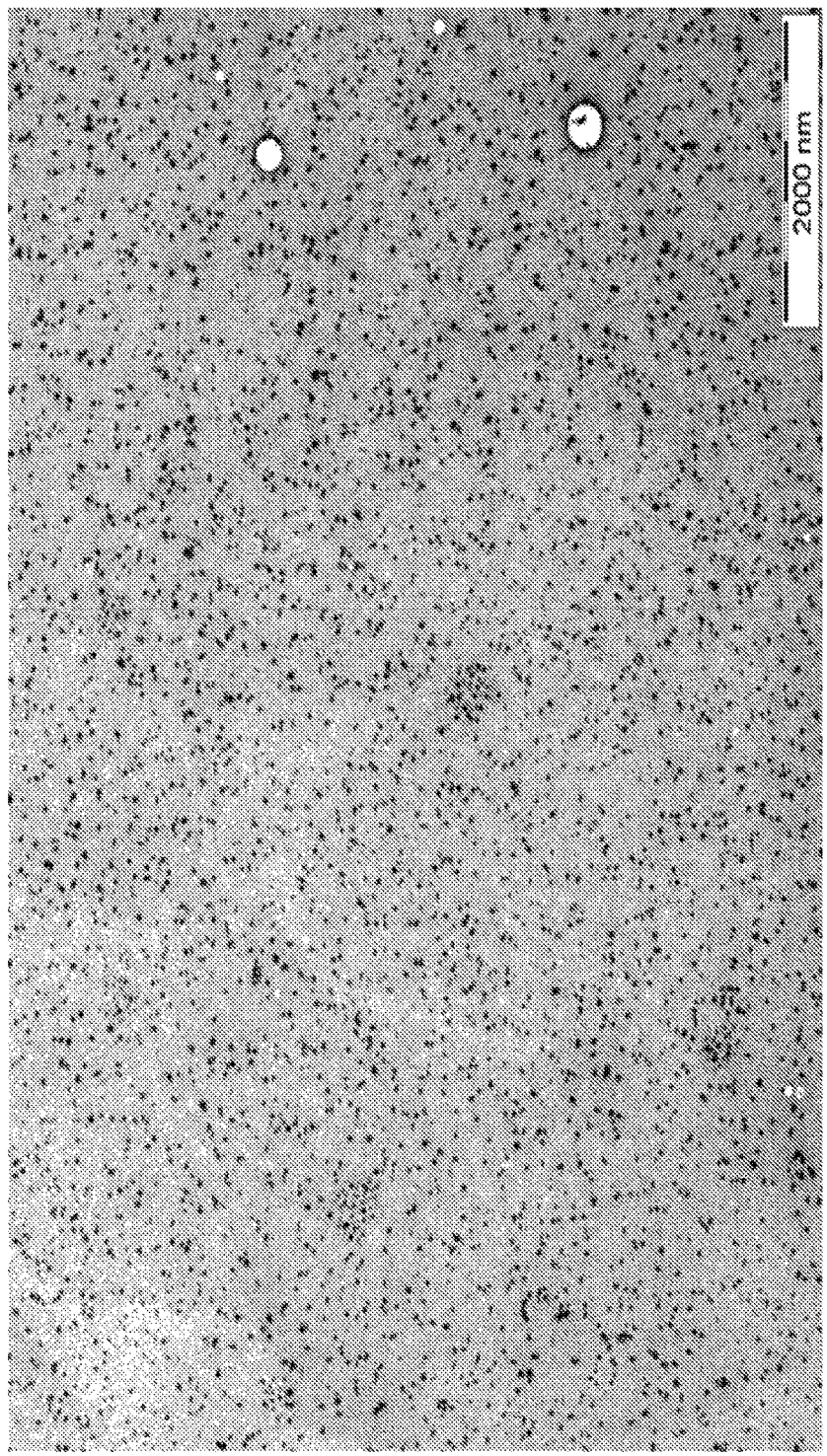
FIG. 8 provides a transmission electron microscopy image of one embodiment of the invention.
Figure 9A:
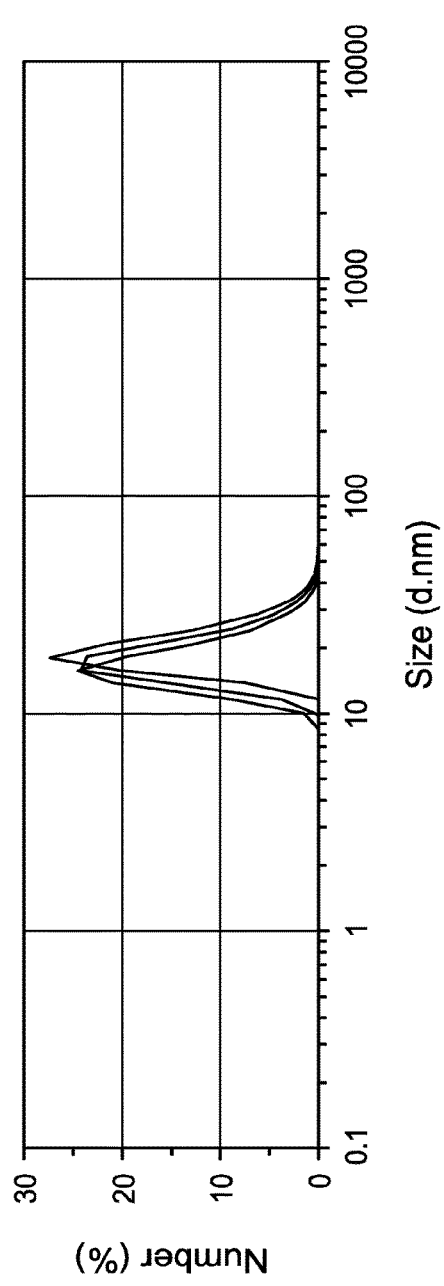
FIG. 9a provides a measure of average particle size of one embodiment of the invention.
Figure 9B:
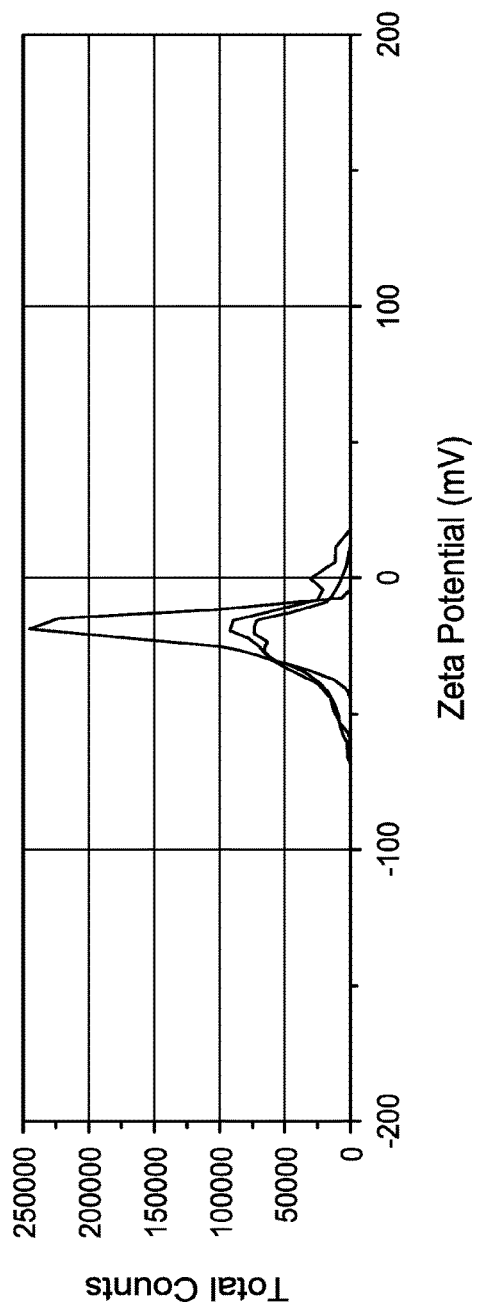
FIG. 9b provides a measure of the zeta-potential of one embodiment of the invention.

A-NP Characterization. Carbon A-NP nanoparticles were prepared by the two-step process described above. In general, as determined by TEM measurements and shown in FIG. 8, the approximately size of the resulting carbon nanoparticles prepared hydrothermally using glucose as the precursor ranges between about 30 nm-50 nm. This is in agreement with the average particle size obtained from dynamic light scattering (DLS) measurements of 40 nm, as shown in FIG. 9a. Referring now to FIG. 9b, the A-NP carbon nanoparticles exhibit a net surface charge of −25 mV and fluoresce at a wavelength of 365 nm.

Figure 10:
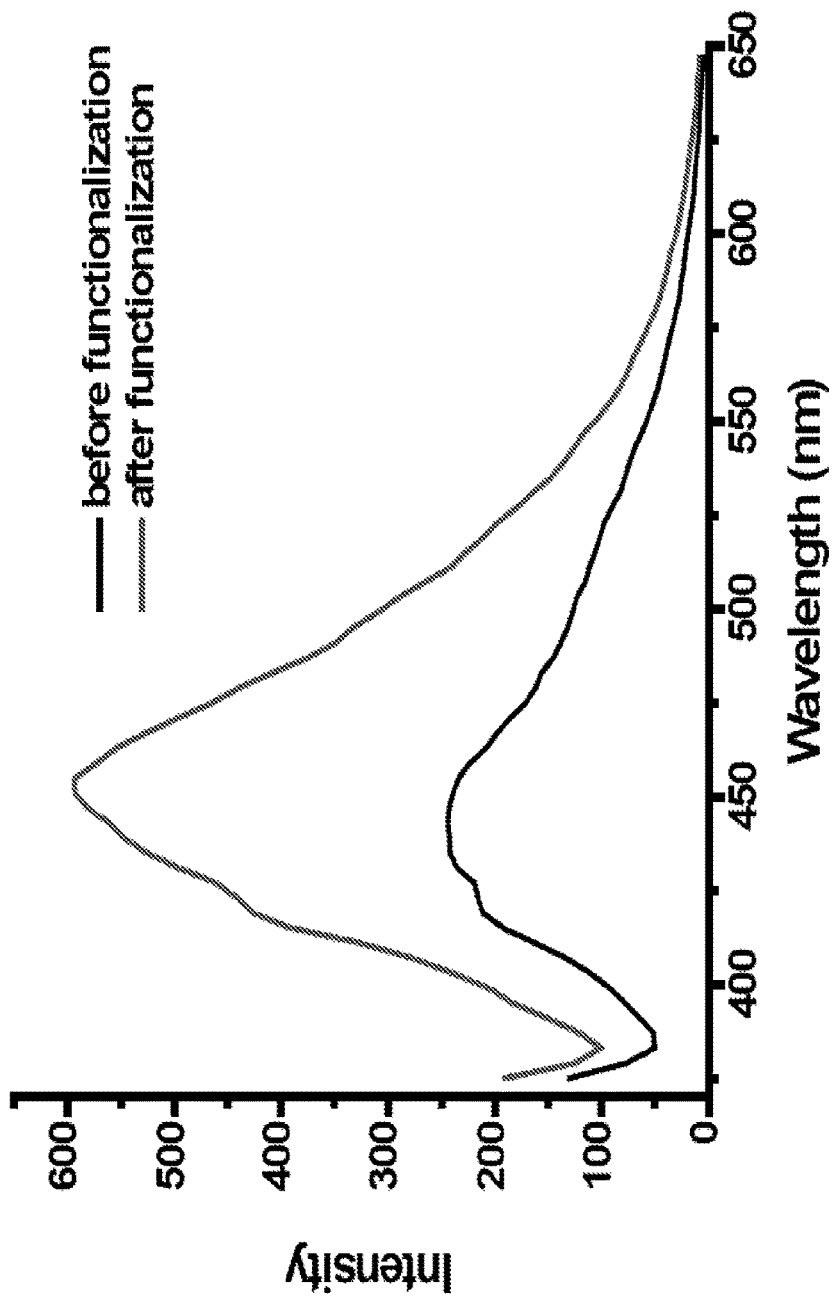
FIG. 10 provides the fluorescence measure of one embodiment of the invention.
Figure 11A:
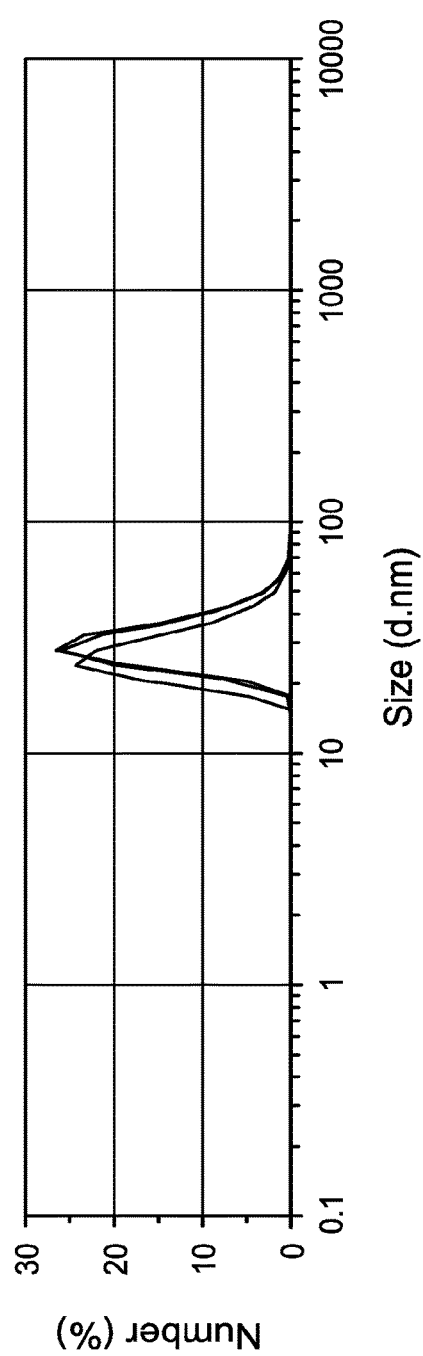
FIG. 11a provides a measure of average particle size of one embodiment of the invention.
Figure 11B:
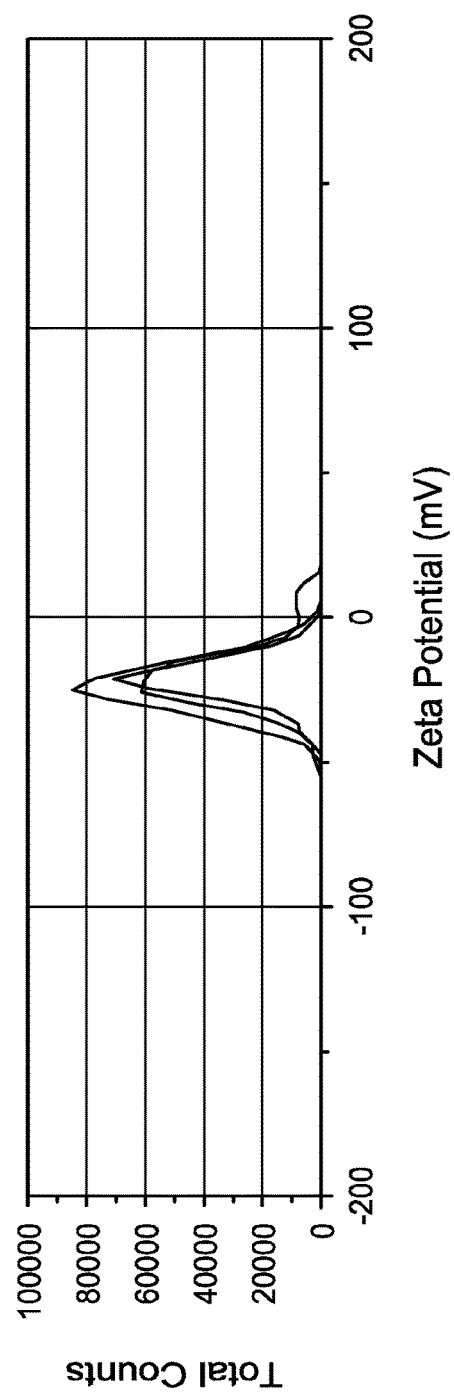
FIG. 11b provides a measure of the zeta-potential of one embodiment of the invention.

In certain embodiments, to increase the fluorescent intensity of the nanoparticles, the as-prepared carbon nanoparticles were refluxed with a solution of ethanolamine to attach the functional group to the surface of the nanoparticles. Referring to FIG. 10, the photoluminescence spectrum shows that the ethanolamine functionalized samples have greater fluorescent intensity as compared to nanoparticles that lack the surface treatment. The top trace is the emission spectrum of the carbon nanoparticles before functionalization, while the lower trace is the spectrum produced by the functionalized carbon nanoparticles. As shown in FIG. 11a, DLS measurements show an average particle size of about 50 nm, suggesting that the surface treatment does not lead to any particle agglomeration. Referring to FIG. 11b, the surface charge of the surface functionalized particles is approximately −21 mV.

Coreflood tests were run using a modular Coretest CFS-830 coreflood system with high salinity brine having a concentration of about 120,000 ppm TDS (total dissolved solids) as a base and displacement fluid. At the start of the test, simple dispersion tests of the A-Dots were run at room temperature using high permeability reservoir rock samples. The dispersion tests used two consecutive tests of a tracer flood (or transmission test), followed by a tracer flush (or mobilization test). The tracer flood included the steps of continuously injecting a solution that included the tracer particles into one end of the core and monitoring the effluent from the other end of the core, until the concentration of the effluent was the same level as the concentration of the tracers being injected into the core. The flush test involved continuously injecting a brine solution into the same inlet end of the core until a tracer concentration of zero was measured at the effluent end of the core.

Figure 12:
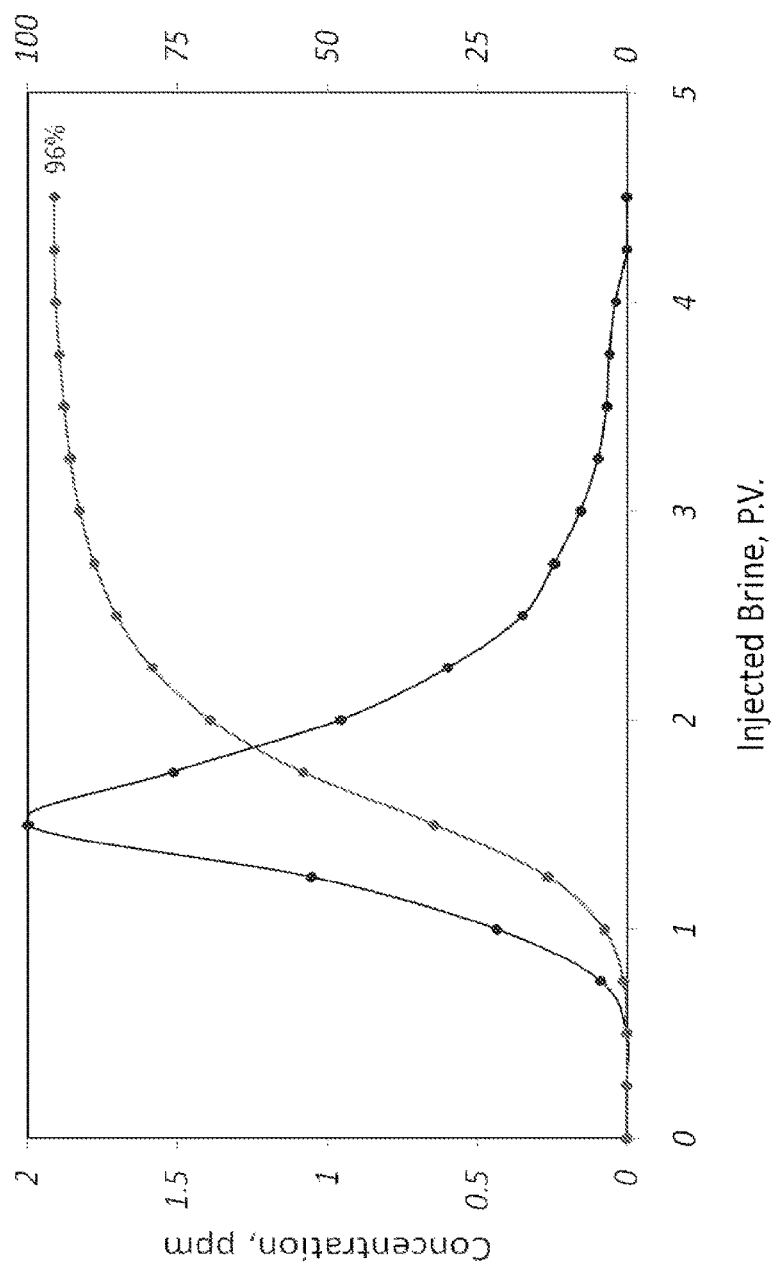
FIG. 12 provides coreflood test results for one embodiment of the present invention.

Tests were conducted using low permeability composite core plugs, which were subjected to more stringent and realistic testing conditions in terms of reservoir temperature, slug volume and saline concentration. The tests included the use of multiple core plugs in series, low permeability plugs (10 millidarcy (mD) or less), high temperature (e.g., greater than about 95° C.), high pressure (e.g., greater than about 3000 psi), and high salinity conditions (e.g., 120,000 ppm or greater). The process included the following steps: first, the core was pre-saturated with saturated brine solution (120,000 TDS) and maintained at a reservoir temperature (approximately 95° C.) and pressure (approximately 3,000 psi) conditions for a few hours. An aqueous solution that included the A-Dots (10 ppm) was injected in an amount equivalent to about 0.2 core pore volumes (or approximately 20%), and shut-in the setup at these conditions for a few days. Following the shut-in period, the core was flushed by injecting a high salinity brine having a TDS of about 120,000 at the same end to which the A-Dots were initially introduced. During testing, effluent from the core sample was monitored by collecting approximately 4-5 mL samples to a fraction collector and conducting fluorescence spectroscopy analyses. Referring to FIG. 12, transport mobility response of the A-Dots following one such test is provided. A composite core plug made of two carbonate rock samples having similar petrophysical properties (including an average brine permeability of 9.89 mD, average porosity of 20.3%, and a total pore volume of 18.74 mL for the two core plugs) was examined. The test employed a 3.8 mL slug of approximately 10 ppm (0.001% w/w) A-Dots solution, amounting to approximately 20% of the total pore volume of the composite core. The test used equal injection rates for both the A-Dots solution and the overflush brine solution at injection rates of about 0.1 mL/min. This procedure created a piston like drive during the slug injection phase and better emulated the rate at which a water flood front moves into the reservoir during the mobilization (flushing) phase of the test. The experiment was shut-in for two (2) days following injection and the slug was at a maintained temperature of about 95° C. FIG. 12 shows an excellent A-Dot recovery factor, exceeding about 95%, following the injection of approximately 4.5 pore volumes of clear brine. This further emphasizes the excellent transport mobility of the A-Dots in the Arab-D medium.

In a large scale field experiment, approximately 5 kg of A-Dot nanoparticles were disposed in about 255 barrels (bbl) of injection water. The solution was mixed on site by recirculating water in the tank at a rate of about 5 bpm (barrels per minute) to provide a 130 ppm solution of A-Dot tracers. A column full of diesel (120 bbl) was then injected into the wellbore as a soaker. The well was shut-in for 1 hr and flowed for 1.5 hr to clean the wellbore and remove any accumulated oil at the top of the formation. The water containing the A-Dots was injected at a rate of about 3 bpm and the injection pressure did not exceed 1500 psi. This step was followed with a column full of normal injection water as an overflush and a column of diesel to serve as a displacement fluid. The invaded zone was estimated to be about 15 ft.

For the production phase, the well was shut-in for 2 days before it was flowed to a gas-oil separator and fluid samples were collected at the wellhead in an attempt to monitor and gauge the nanoparticles' stability and potential for recovery. After recovery, fluorescence measurements showed overall A-Dots recovery on the order of at least about 80%, alternatively at least about 85%, alternatively at least about 90%.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these references contradict the statements made herein.

That which is claimed is:

1. A fluorescent nanoagent for use in a subsurface petroleum reservoir, the nanoagent comprising:
   a carbon-based nanoparticle core, said nanoparticle core having an average diameter of less than 100 nm;
   wherein said nanoparticle core includes a plurality of functional groups appended to the surface thereof; and
   wherein the fluorescent nanoagent is produced from a solution comprising a sugar, an amino alcohol and deionized water reacted under conditions capable of synthesizing the fluorescent nanoagent.

2. The fluorescent nanoagent of claim 1, wherein the carbon-based nanoparticle core has an average diameter between 10 nm and 50 nm.

3. The fluorescent nanoagent of claim 1, wherein the fluorescent nanoagent is detectable at a concentration of 0.01 ppm.

4. The fluorescent nanoagent of claim 1, wherein the functional groups appended the surface of the fluorescent nanoagent can be excited at a wavelength between 400 nm and 500 nm.

5. The fluorescent nanoagent of claim 1, wherein the functional group appended to the surface of the nanoparticle core is an amino alcohol.

6. The fluorescent nanoagent of claim 1, wherein the functional group appended to the surface of the nanoparticle core is selected from methanolamine, ethanolamine, and propanolamine.

7. The fluorescent nanoagent of claim 1, wherein the functional group appended to the surface of the nanoparticle core is ethanolamine.

8. The fluorescent nanoagent of claim 1, wherein the functional group is appended to the surface of the nanoparticle core is appended with an amide linkage.

9. The fluorescent nanoagent of claim 1, wherein the sugar is selected from the group consisting of glucose and fructose.

10. The fluorescent nanoagent of claim 1, wherein the amino alcohol is selected from the group consisting of methanolamine, ethanolamine, and propanolamine.

11. The fluorescent nanoagent of claim 1, wherein the fluorescent nanoagent is stable at a temperature of 100° C. to 200° C.

12. The fluorescent nanoagent of claim 1, wherein the fluorescent nanoagent is stable at a salinity concentration of 75,000 ppm to 120,000 ppm.

13. The fluorescent nanoagent of claim 1, wherein the plurality of functional groups appended to the surface of the nanoparticle core is ethanolamine, the sugar is glucose, and the amino alcohol is ethanolamine.

14. A fluorescent nanoagent for use in a subsurface petroleum reservoir, the nanoagent comprising:
   a carbon-based nanoparticle core, said nanoparticle core having an average diameter of less than 100 nm;
   wherein said nanoparticle core includes an ethanolamine functional group appended to the surface thereof; and
   wherein the fluorescent nanoagent is produced from a solution comprising glucose, ethanolamine and deionized water reacted under conditions capable of synthesizing the fluorescent nanoagent.

* * * * *